(12) United States Patent
McElroy

(10) Patent No.: US 11,684,531 B1
(45) Date of Patent: Jun. 27, 2023

(54) TRAY LIFT AUTOPSY TABLE AND SYSTEM

(71) Applicant: MCCLAREN, WILSON & LAWRIE, INC., Ashland, VA (US)

(72) Inventor: Russell H. McElroy, Doswell, VA (US)

( * ) Notice: Subject to any disclaimer, the term of this patent is extended or adjusted under 35 U.S.C. 154(b) by 626 days.

(21) Appl. No.: 16/602,452

(22) Filed: Oct. 8, 2019

Related U.S. Application Data

(60) Provisional application No. 62/766,275, filed on Oct. 11, 2018.

(51) Int. Cl.
*A61G 13/00* (2006.01)
*A61G 13/06* (2006.01)
(Continued)

(52) U.S. Cl.
CPC .......... *A61G 13/0027* (2013.01); *A61B 16/00* (2013.01); *A61G 1/02* (2013.01); *A61G 13/02* (2013.01); *A61G 13/06* (2013.01)

(58) Field of Classification Search
CPC .... A61G 13/0027; A61G 13/02; A61G 13/06; A61G 1/02; A61B 16/00
See application file for complete search history.

(56) References Cited

U.S. PATENT DOCUMENTS

| | | | |
|---|---|---|---|
| 2,022,714 A * | 12/1935 | Gallup | A61G 13/0027 5/606 |
| 2,739,785 A | 3/1956 | Gray | 254/93 |
| 4,101,120 A | 7/1978 | Seshima | 5/616 |

(Continued)

FOREIGN PATENT DOCUMENTS

| | | | | |
|---|---|---|---|---|
| CN | 207506739 U | * | 6/2018 | |
| CN | 108888458 A | * | 11/2018 | ......... A61G 13/0027 |

(Continued)

*Primary Examiner* — David R Hare
*Assistant Examiner* — Alexis Felix Lopez
(74) *Attorney, Agent, or Firm* — Douglas J. Ryder; Ryder, Mazzeo & Konieczny LLC

(57) ABSTRACT

A system deployable in post-mortem rooms and other facilities for facilitating medical examinations, including autopsies. A system as described includes a corpse-receiving station and an organ dissecting station, each being in some embodiments substantially rectangularly shaped and having a longest length dimension. The corpse-receiving station and organ dissecting station are in some embodiments arranged so their longest length dimensions are oriented substantially perpendicularly, having a formation resembling an L-shape when viewed from an overhead perspective. A system of the instant technology eliminates the necessity for pathologists and technicians of having to lift a subject or corpse, by virtue of the corpse-receiving station being configured and equipped to be selectively height-adjustable, which also eliminates the need for step-stools and the like. Moreover, the organ dissecting station is configured and equipped to be selectively height-adjustable and selectively adjustable laterally with respect to its base. The combination of the features and elements provided enables 360 degree access to a corpse residing on the corpse-receiving station, while greatly lessening un-necessary walking and essentially eliminating hazards associated with biological fluids falling onto the floor surface of the work area. Hygiene is increased by provision of a ventilation system integrated into the components of systems provided herein.

21 Claims, 20 Drawing Sheets

(51) Int. Cl.
*A61B 16/00* (2006.01)
*A61G 1/02* (2006.01)
*A61G 13/02* (2006.01)

(56) References Cited

U.S. PATENT DOCUMENTS

| | | | |
|---|---|---|---|
| 4,155,471 A | 5/1979 | Yancy | 414/420 |
| 4,650,171 A | 3/1987 | Howorth | 5/600 |
| 4,794,655 A | 1/1989 | Ooka et al. | 5/81.1 C |
| 4,980,956 A * | 1/1991 | Fischer | A61G 13/0027 27/21.1 |
| 5,123,797 A | 6/1992 | Schnelle et al. | 414/401 |
| 5,163,189 A | 11/1992 | DeGray | 5/86.1 |
| 5,244,433 A * | 9/1993 | Utterback | A61G 13/108 5/606 |
| 5,477,570 A | 12/1995 | Hannant et al. | 5/86.1 |
| 5,621,932 A | 4/1997 | Strachan | 5/600 |
| 7,137,161 B2 | 11/2006 | Hempker et al. | 5/611 |
| 7,774,873 B2 | 8/2010 | Martin et al. | 5/81.1 R |
| 2017/0360639 A1 * | 12/2017 | Corona | G08B 3/10 |

FOREIGN PATENT DOCUMENTS

| | | | | |
|---|---|---|---|---|
| CN | 208145146 U | * | 11/2018 | |
| CN | 208838453 U | * | 5/2019 | |
| CN | 208838456 U | * | 5/2019 | |
| CN | 212490604 U | * | 2/2021 | |
| CN | 113397892 A | * | 9/2021 | |
| FR | 2786091 A1 | * | 5/2000 | A61G 1/0212 |
| JP | 2007244762 A | * | 9/2007 | |
| WO | WO-9945881 A1 | * | 9/1999 | A61G 13/0027 |

* cited by examiner

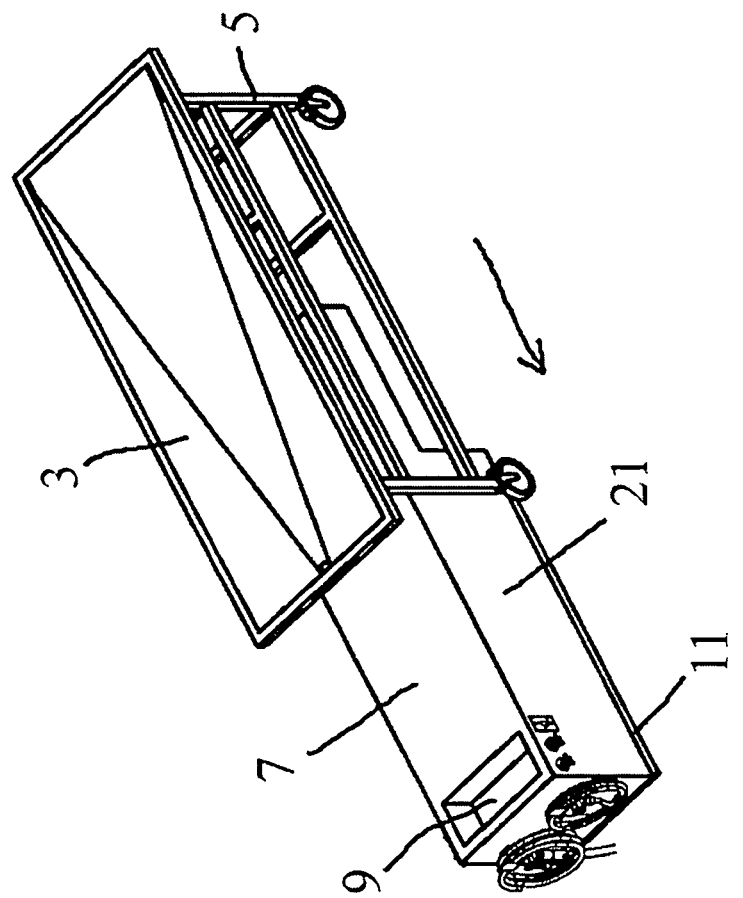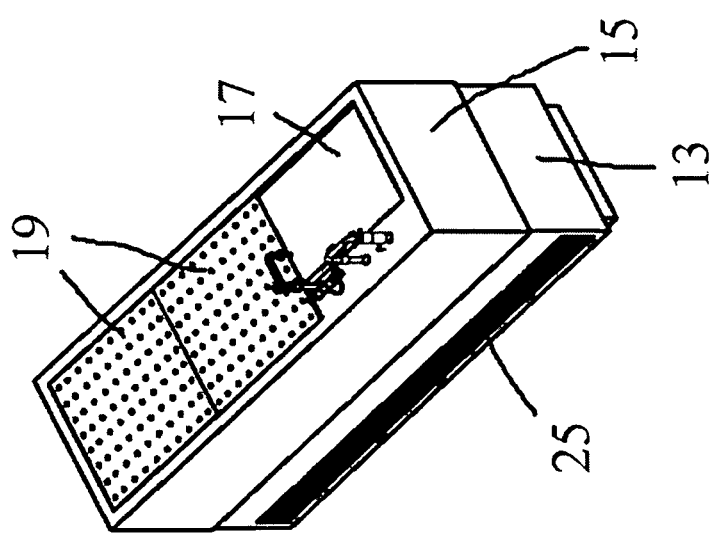
FIG. 2

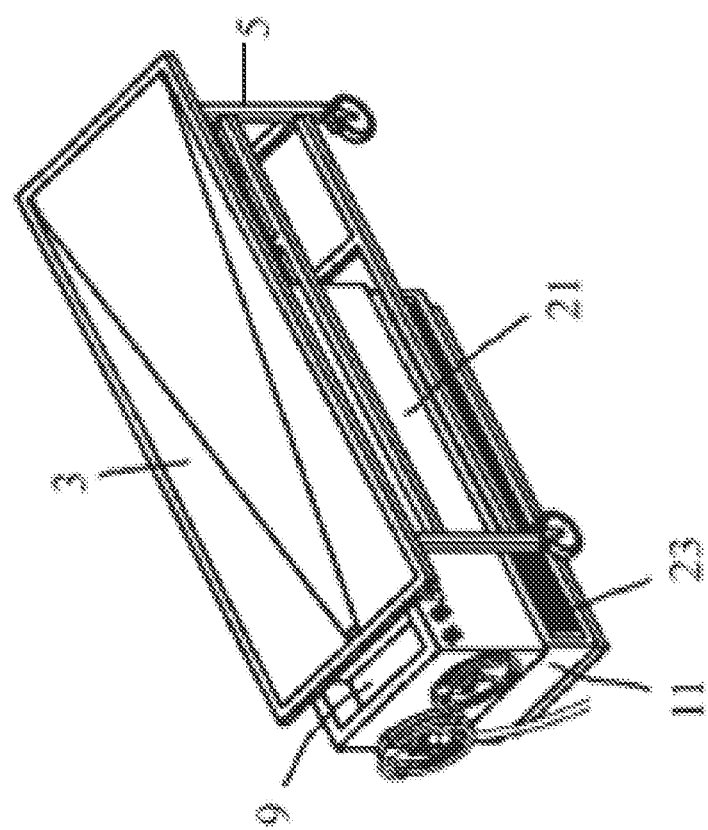
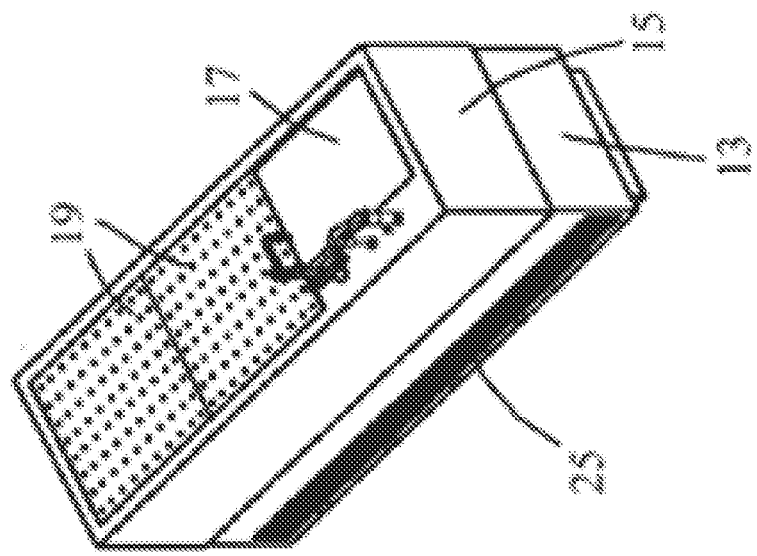
FIG. 4

TRAY LIFT AUTOPSY TABLE AND SYSTEM

TECHNICAL FIELD

This invention relates generally to forensic pathology. More particularly, it relates to equipment and wares associated with the process and steps involved with the autopsy of a mammalian corpse, including without limitation, human corpses.

BACKGROUND OF THE INVENTION

The statements in this background section merely provide background information related to the present disclosure, and may not constitute prior art.

The examination of a human corpse is an important facet of forensic and medical examinations. It is common practice for medical examiners to employ an autopsy table, which is simply a table upon which a corpse is disposed for the purpose of enabling medical personnel to have access to various portions of the subject corpse.

Workers in this field have provided various advances in the art concerning autopsy tables. Indeed, the most well-known and long established autopsy table consists of a simple ceramic slab, having no provision for exhausting air from around the corpse. Some advancements were made in the art by providing stainless steel tabletop surfaces having a plurality of perforations disposed therethrough, the volume beneath the perforated tabletop surface being subjected to reduced pressure such as by the presence of a blower fan ventilation system, which draws ambient air through the plurality of holes in the perforated tabletop surface.

One issue which personnel working in a post-mortem room are faced with, is that corpses are typically delivered to a post-mortem room on a wheeled structure, which is often a gurney. This necessitates a requirement that a corpse must be removed from the gurney and re-located atop the autopsy table. When proceeding according to current or conventional technology, this re-location of the corpse must be undertaken manually, essentially requiring two persons to lift the corpse from the gurney and place it on the autopsy table. This task can be further complicated by the increasing weight of the typical human body.

Another issue in the art, is that workers associated with the autopsy process need to be able to move about themselves, to inspect different portions of the corpse from different angles or perspectives, including when dissections are performed. Often, the autopsy practitioner finds it necessary to elevate themselves from the floor surface of the post-mortem room, in order to dispose themselves at a location or perspective that is most beneficial for the task being performed. In bariatrics cases, the corpse may be as high as 24 inches when laying flat on the back. This often requires the use of step-stools, or other functionally-equivalent articles for gaining perspective advantage, which hinders the safety of the pathologist or investigator.

In addition, an autopsy table must necessarily permit a practitioner full 360 degree access about the autopsy table, to enable a full analysis of a subject corpse.

In some of the more popular configurations, conventional modern autopsy tables actually employ two separate tables. The first comprises the tabletop surface upon which the corpse rests, and the second is known as the organ dissecting station. In a typical setup, the top surfaces of each of these are generally rectangular in shape, and are arranged to be in an "L" shape, for purposes of economy for the practitioner being able to remove an organ from the corpse and immediately place it on the surface of the dissecting station, without having to travel any substantial distance, while dripping serological fluid onto the floor. When using conventional autopsy tables, one problem arises, since it is highly desirable for the practitioner to have 360 degree access to a subject corpse, and the L-shaped configuration prohibits the practitioner from having such 360 degree access to a corpse, requiring extra walking and maneuvering.

Further, in a typical autopsy, most or all of the bodily internal organs are removed from the corpse, including the heart, liver, spleen, lungs, etc. Following removal, the examiner manually transfers the organs to a scale or to another surface for temporary storage. During the transfer, it often occurs that bodily fluids, residues and other biomaterial will drip from the organ under the influence of gravity, and land on the floor of the post-mortem room. This can create a slipping hazard for personnel, in addition to being a source of long-term biomaterial buildup, leading to potentially unsafe working conditions and requiring significant clean-up after each autopsy.

SUMMARY OF THE INVENTION

In some embodiments of the disclosure are provided a system useful for performing medical examinations. Such systems comprise a corpse-receiving station having a longest length dimension, an end and an edge, a base portion and an upper portion. The upper portion has a flat top surface, and is selectively vertically-adjustable with respect to the base portion. There is an organ dissecting station having a longest length dimension, an end and an edge, a base portion, and an upper portion having a top surface. The upper portion of the organ dissecting station is selectively vertically-adjustable with respect to the base portion, and is further selectively horizontally-adjustable with respect to the base portion. The corpse-receiving station and the organ dissecting station are disposed in close proximity to one another substantially as shown and described with respect to the drawings provided herewith, and oriented so that the longest length dimension of the corpse-receiving station and the longest length dimension of the organ dissecting section intersect one another at any selected angle in the range of between seventy (70) and one hundred ten (110) degrees.

Also provided are methods for examining and dissecting a corpse. In some embodiments, the methods comprise the steps of first providing a system according to some embodiments of the instant technology, including a gurney assembly having a tray disposed thereon and the tray further comprising a corpse disposed thereon. The gurney assembly is wheeled sufficiently to provide the tray to be disposed above the top surface of the corpse-receiving station. The upper portion of the corpse-receiving station is sufficiently elevated to lift the tray from the wheeled base. Then, the wheeled base is removed from its being disposed about the corpse-receiving station, by wheeling it away. The corpse is examined with respect to any pertinent feature normally associated with corpses by pathologists. The upper portion of the organ dissecting section is at some selected point in time caused to be moved horizontally, sufficiently to create an opening space between the organ dissecting section and the corpse-receiving section of sufficient dimension to enable the pathologist to pass through the space. A pathologist subsequently can pass through the space and further examine the corpse. Examining the corpse can include making at least one incision on the corpse, as well as the removal of any organ of the corpse selected by the pathologist.

BRIEF DESCRIPTION OF THE DRAWINGS

The drawings shown and described herein are provided for illustration purposes only and are merely exemplary of different embodiments provided herein, not intended to be construed in any delimitive fashion.

FIG. 2 a perspective view of components of a system according to some embodiments;

FIG. 4 is a perspective view of components of a system according to some embodiments;

FIG. 19 is a side elevation view of a framework useful in providing a gurney assembly for some embodiments.

DETAILED DESCRIPTION

The following description is merely exemplary in nature and is in no way intended to limit the present disclosure, application, or uses.

Figure 1:
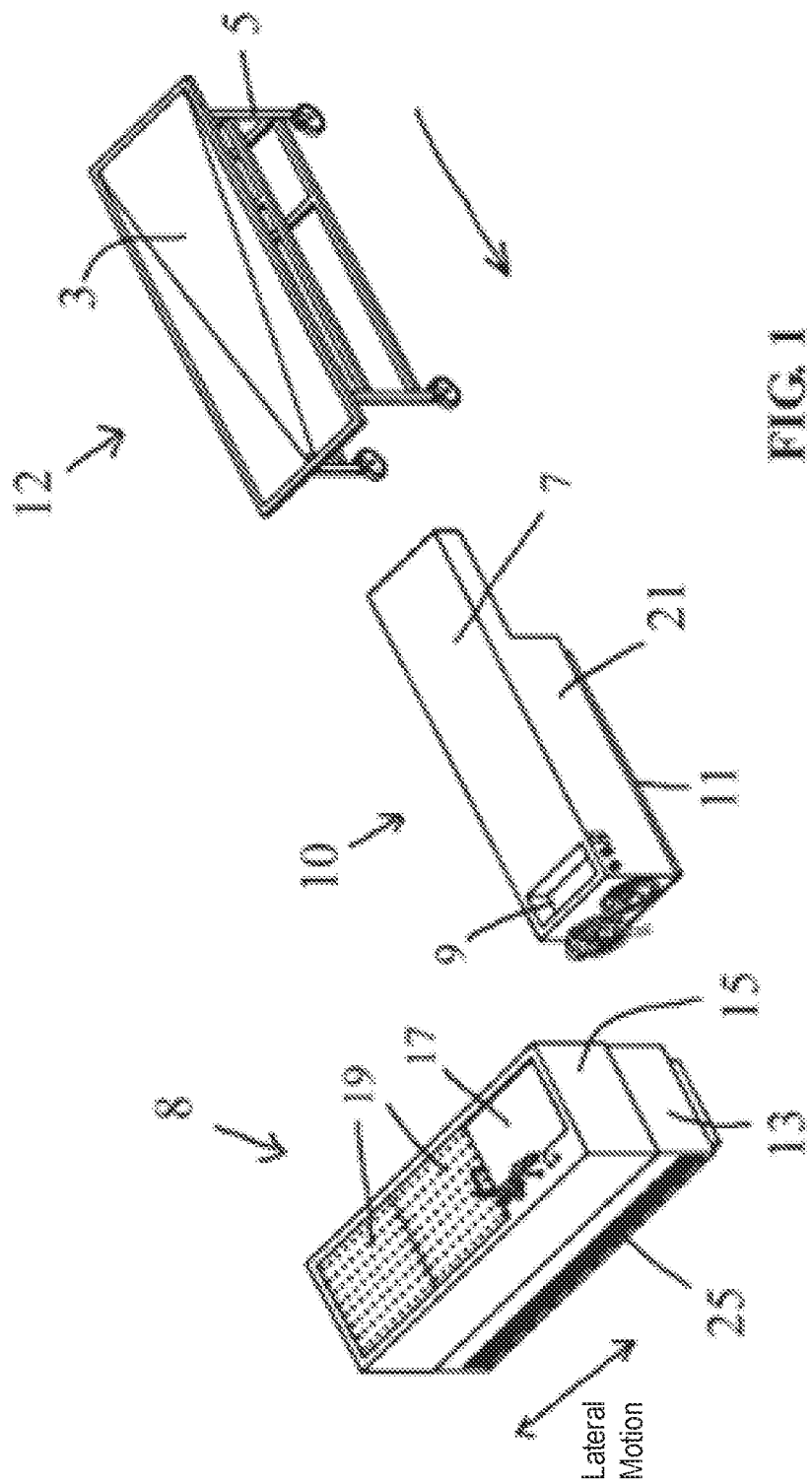
FIG. 1 is a perspective view of components of a system according to some embodiments.

Referring now to the drawings, and initially to FIG. 1, there are shown a plurality of components of a system according to some embodiments of the instant technology. There is a gurney assembly 12, which in some embodiments consists generally of a tray 3 which is removably disposed upon a wheeled base 5. Tray 3 is generally planar, and in some embodiments comprises a raised lip or its functional equivalent disposed about its perimeter, so as to contain any fluid materials. Tray 3 is comprised of a rigid material of sufficient thickness to support a human or other mammalian corpse without deforming by any substantial amount. In some embodiments, tray 3 is comprised of metallic elements or known alloys. In other embodiments, tray 3 is comprised of any stainless steel, with medical grade stainless steel being selected. In optional embodiments, tray 3 is comprised of any suitable composite material.

There is a corpse receiving station 10, which is generally comprised a stationary base portion 11 which resides on the floor of the work area, and a height-adjustable upper portion 21. Upper portion 21 of corpse receiving station 10 has a flat or substantially-flat top surface 7, and in some embodiments includes a basin 9 having a drain which is connected with a sewer or other liquid discharge line. In some embodiments, the surface 7 of the receiving station 10 is sloped to basin 9 to facilitate serological drainage to the basin during autopsy and clean-up. In some embodiments, base portion 11 is provided with a ventilation system for moving ambient air. Such ventilation system is termed a downdraft ventilation system, and has its inlet air provision disposes all about the perimeter of base portion 11, with the evacuated air being directed into ductwork which is selected to be present beneath the floor of the post-mortem room, and which is ventilated to the outside air.

There is also an organ dissecting station 8, which includes a stationary base portion 13, to which is attached a moveable upper portion 15. Moveable upper portion 15 and base portion 13 are configured and equipped to provide moveable upper portion 15 the ability to have its position adjusted in two different modes, independent of one another. The first mode is vertical motion, as was the same for upper portion 21 of corpse receiving station 10. However, in some embodiments moveable upper portion 15 is also provided with capability of lateral motion, in the directions indicated by the double arrow in FIG. 1, independently of the height position of upper portion 15 with respect to base portion 13. For purposes of this description, lateral motion is horizontal motion, parallel to the longest length dimension of organ dissecting station 8, and in either possible direction, as selected.

In some embodiments at the top surface of upper portion 15 there are disposed panels 17, 19, whose positions are interchangeable. In some embodiments, these panels reside on a recessed lip built in to the upper portion, upon which the panels reside. Panels 19 in some embodiments comprise a perforated sheet material, such as perforated stainless steel. Their thickness is any thickness in the range of between about two millimeters and 15 millimeters, including all thicknesses therebetween. This feature is useful for embodiments in which organ dissecting station 8 is equipped internally with a ventilation system having an air inlet, an air pump, and an effluent air outlet which vents into the floor of the post-mortem room and ultimately to the outside. In some embodiments, an air exhaust system is present in the building in which the autopsy room is housed at a remote location, and ducting is provided from such system to beneath the autopsy table, thereby withdrawing room air into the building's ventilation system. In such embodiments, the air inlet is disposed about the perimeter of base portion 13 but also provides for a negative pressure to be present within the confines of moveable upper portion 15, such that ambient air is drawn in through the perforations of panels 19. This is helpful when a bodily organ is temporarily disposed on either of panels 19, as gases and vapors are evacuated from the area. Panel 17 in some embodiments has no perforations, and is suitable for placement of a mass balance or other type of scale thereon, for use in weighing bodily organs. The respective locations of panels 17, 19 can be interchanged based on the desires or needs of a user.

Figure 3:
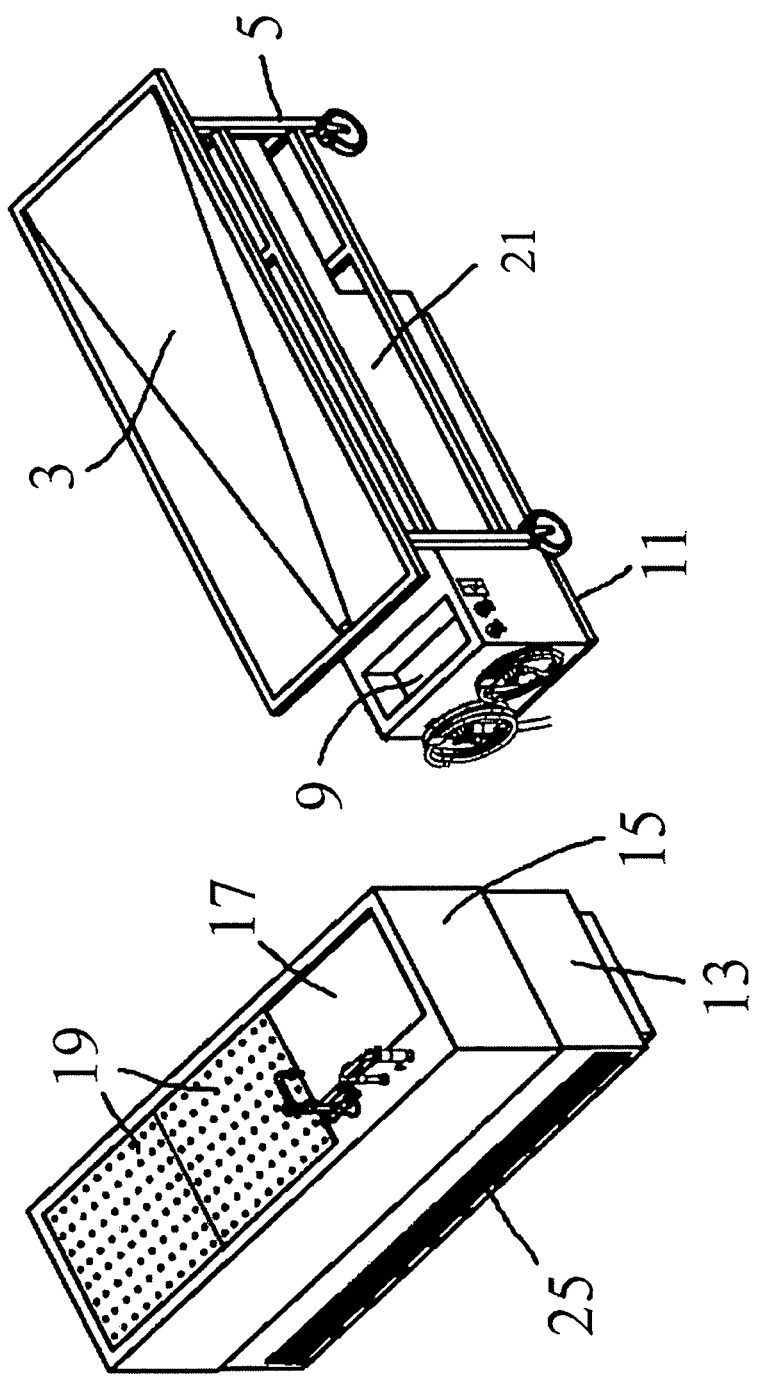
FIG. 3 is a perspective view of components of a system according to some embodiments.
Figure 5:
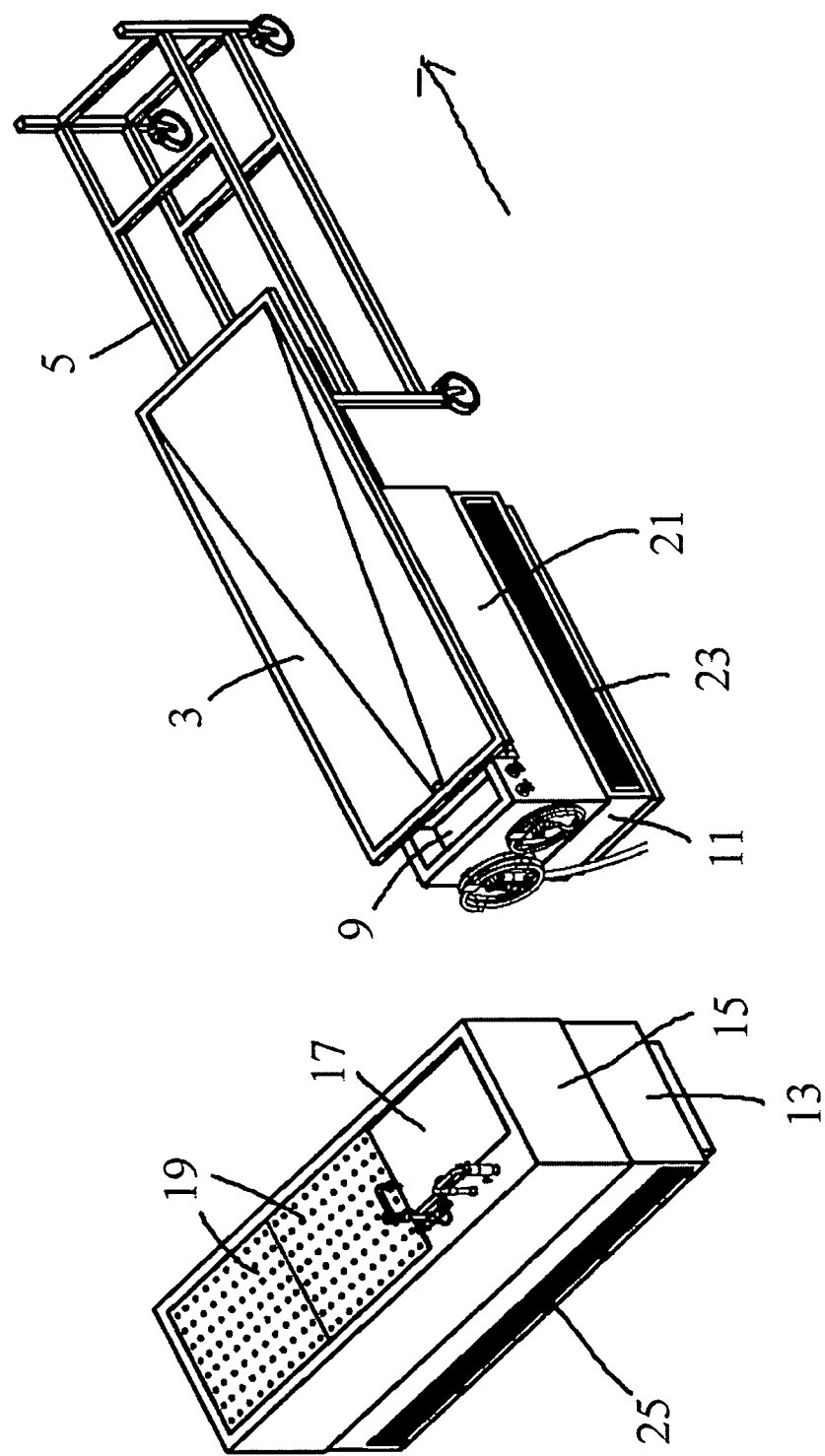
FIG. 5 is a perspective view of components of a system according to some embodiments.
Figure 6:
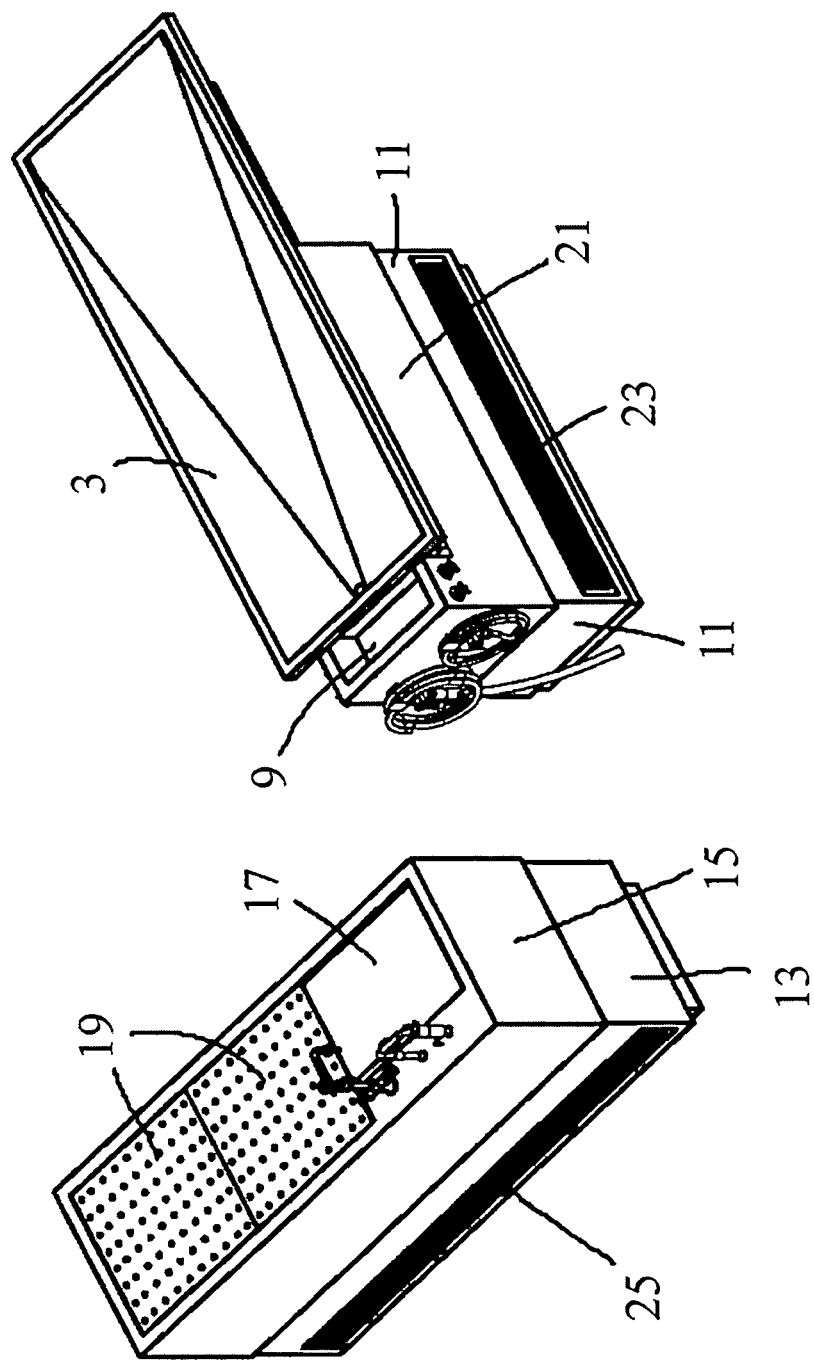
FIG. 6 is a perspective view of components of a system according to some embodiments.

As will be appreciated, the features of the individual components of a system described herein are important, and when disposed as taught herein and employed as taught herein, several new synergistic functions are enabled for the pathologist to take advantage of. To further explain, consideration is directed to the gurney assembly 12 of FIG. 1 and particularly with reference to the arrow depicted thereon. As shown in FIG. 1, the several components are disposed to receive a corpse, which will be present on gurney assembly 12, as it is wheeled in the direction indicated by the arrow. Proceeding to FIG. 2, it is seen that gurney assembly 12 is now partially disposed over the top surface 7 of upper portion 21 of corpse receiving station 10. As gurney assembly 12 is further wheeled in the direction of the arrows shown on FIGS. 1, 2, it eventually reaches a point as shown in FIG. 3 in which tray 3 is completely disposed over top surface 7 (FIG. 1) of upper portion 21 of corpse receiving station 10 (FIG. 1). At this point, a user may elect to energize the corpse receiving station to cause upper portion 21 to become elevated, as shown in FIG. 4. In FIG. 4 can be seen the air intake 23 disposed about a portion of the perimeter of base portion 11, admitting ambient air from the area for purposes of evacuation noxious gases. Further elevation of upper portion 21 causes tray 3 to become lifted off from and detached from wheeled base 5, to the extent that removal of wheeled base 5 from the post-mortem room or area becomes possible, as shown in FIGS. 5, 6.

Figure 7:
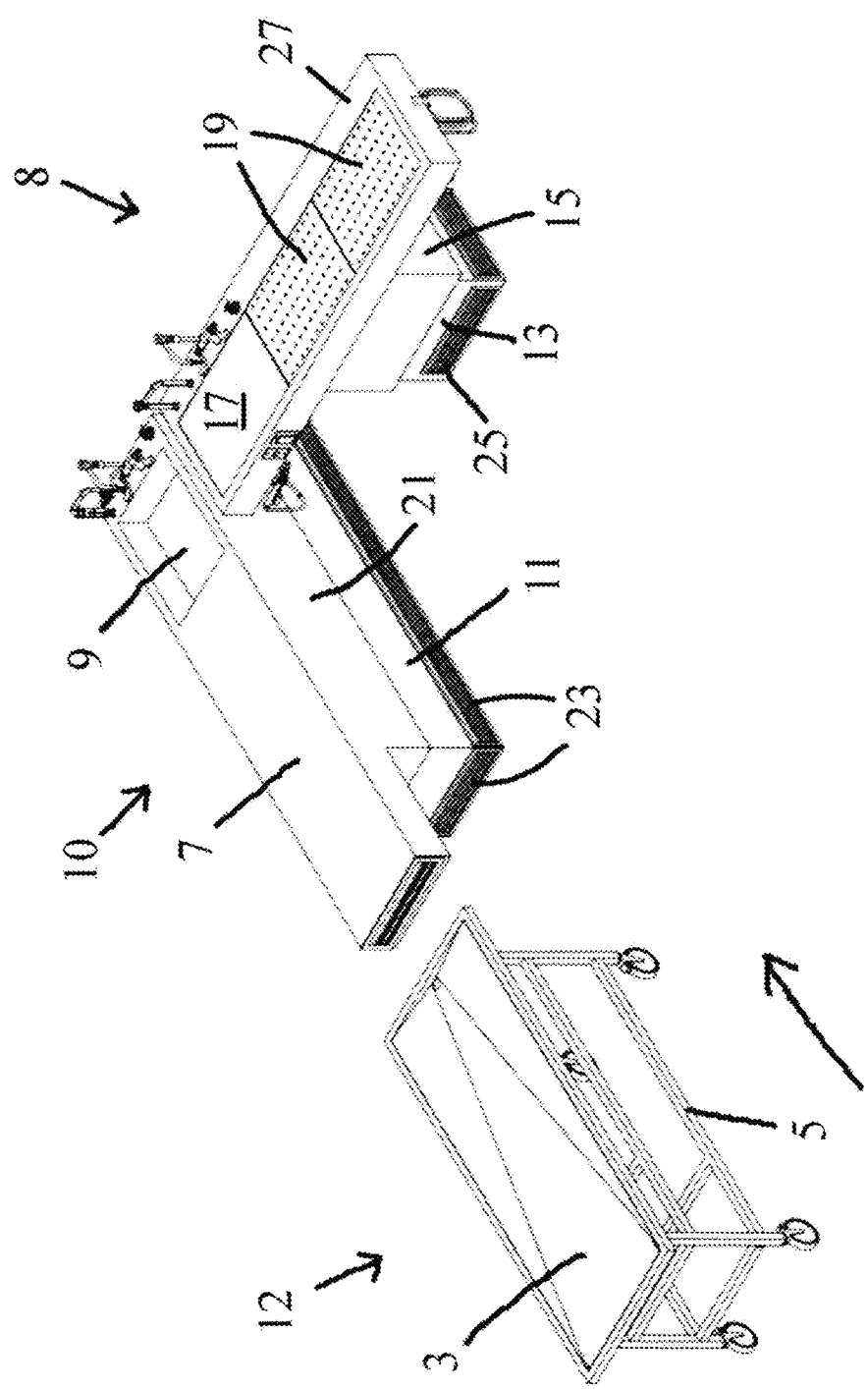
FIG. 7 is a perspective view of components of a system according to some embodiments.

FIG. 7 shows an alternate perspective view of a system according to some embodiments of the instant technology, showing the respective locations of gurney assembly 12, corpse-receiving station 10, and organ dissecting section 8. The system is configured generally as shown; however, the individual components of the organ dissecting station 8 and corpse-receiving station 10 can be slightly moved with respect to one another versus the exact configuration depicted in FIG. 7, provided the functional capabilities as provided herein are maintained. In general, organ dissecting station 8 and corpse-receiving station 10 are configured to appear approximately rectangularly, as viewed from an overhead perspective, each having a longest length dimension, and a width dimension. From an overhead perspective, organ dissecting station 8 and corpse-receiving station 10 are disposed with respect to one another such that each of their longest length dimensions are perpendicular, or substantially perpendicular, as in the letter "L" of the English language, and it is therefore an accurate description for some embodiments that these components can be described as forming a system which is generally L-shaped, as viewed from above.

In FIG. 7 are shown the respective locations of base portion 11, upper portion 21, top surface 7, basin 9 and air intakes 23 of the corpse receiving station 10. The base portion 13, moveable upper portion 15, perforated surfaces 19, panel 17, air intakes 25 and tabletop frame 27 of the corpse-receiving station 8 are also shown. Tabletop frame 27 is generally a tabletop, provided with perimeter lip or flange features sufficient to receive perforated panels 19 and panel 17, these panels being held in place by the force of gravity acting on the panels present in dimensionally-complementary openings on tabletop frame 27, analogous to the configuration of a steam bath in a food-service line, the panels resting on flanges. FIG. 7 depicts gurney assembly 12 comprising tray 3 and wheeled base 5 as being in motion in the direction of the arrow shown, typically under the force and guidance of a human operator or technician, towards the corpse receiving section.

Figure 8:
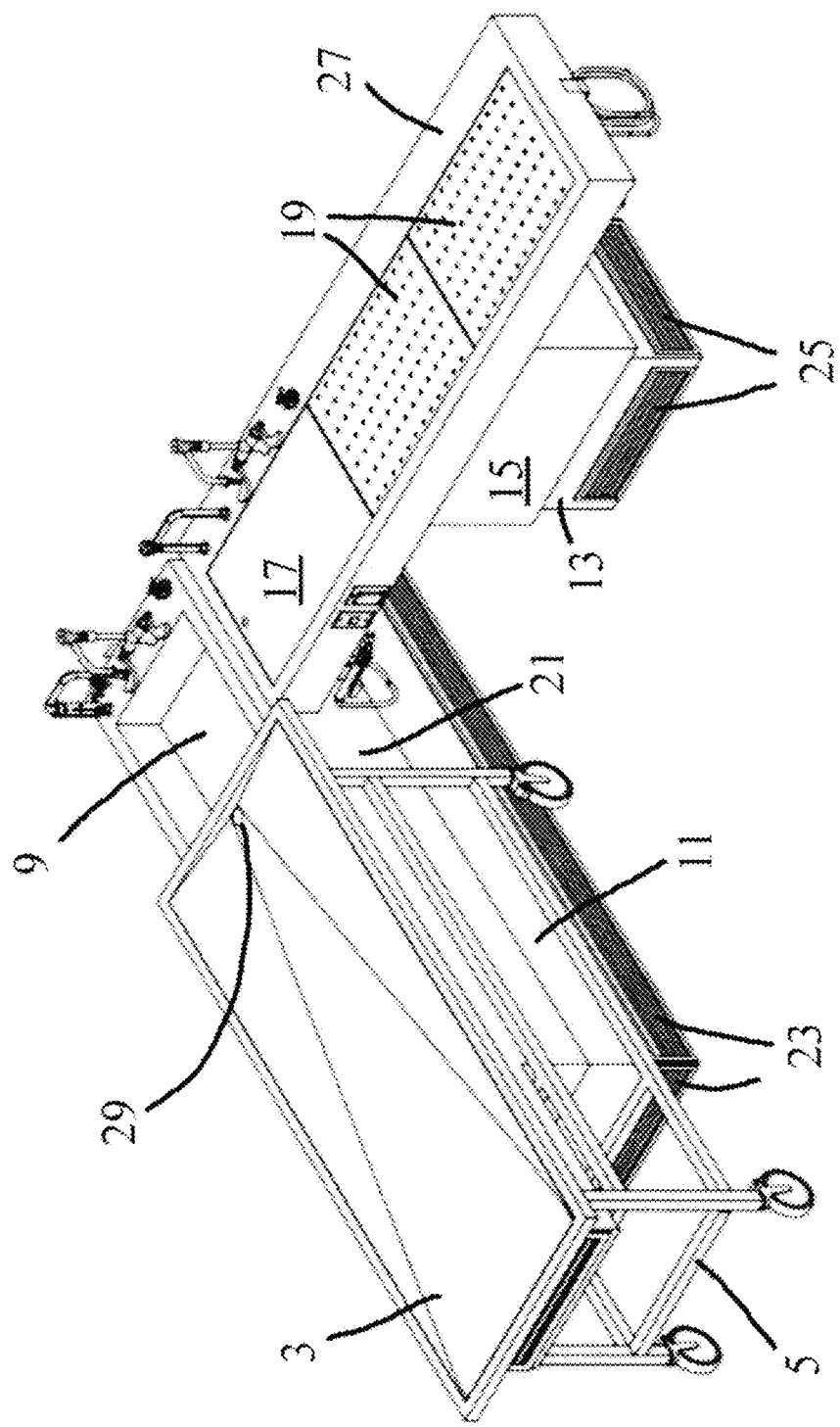
FIG. 8 is a perspective view of components of a system according to some embodiments.

In FIG. 8 are depicted the same components and features as shown and described with reference to FIG. 7, excepting now the gurney assembly is shown as having been moved to be disposed above top surface 7 (FIG. 1) of corpse-receiving station 10 (FIG. 1). In this FIG. 8, the height the top surface 7 (FIG. 1) of upper portion 21 with respect to the floor is seen to be about the same as is the height of the top surface of tabletop frame 27 disposed with respect to the floor. FIG. 8 illustrates some embodiments in which the end of organ dissecting station 8 (FIG. 1) is facing an edge of the corpse-receiving station 10 (FIG. 1), and the edge of organ dissecting station 8 is coincident, with an end of the corpse-receiving station 10. FIG. 8 also shows location of drain hole 29, depicted in other drawings as a circle. In some embodiments, top surface of tray 3 is angled, sloped or otherwise contoured so as to channel or funnel, or otherwise direct any fluid substance present on the top surface of tray 3 to be directed towards drain hole 29 under the influence of gravity. The system herein is configured so a user can locate drain hole 29 over basin 9 to enable fluid substances to pass through drain hole 29 and into basin 9. Towards assisting this function, the vertical supports of wheeled base 5 which support tray 3 can be of sufficiently different heights or lengths, to enable drain hole 29 to be at a lower elevation with respect to the floor. In other words, tray 3 is angled or sloped slightly downwards towards drain hole 29 by virtue of two of the vertical supports of wheeled base 5 being taller than the two vertical supports more proximal to drain hole 29.

Similarly, in some embodiments, the top surface 7 of corpse receiving station 10 is not flat, but is rather angled, the portion distal from basin 9 being at a higher elevation than the portion proximal to basin 9, for the purpose of directing any fluid substance which might be present on top surface 7, towards basin 9. In some embodiments is provided a short wall or lip disposed about the perimeter of top surface 7 for preventing any fluid substance present on top surface 7 from escaping to the floor. In some embodiments, the degree of slope of top surface 7 coincides or substantially coincides with the degree of slope of tray 3 so that these elements surfaces mate somewhat or otherwise coincide when tray 3 is lifted from wheeled base 5 by upper portion 21 as herein described.

Figure 9:
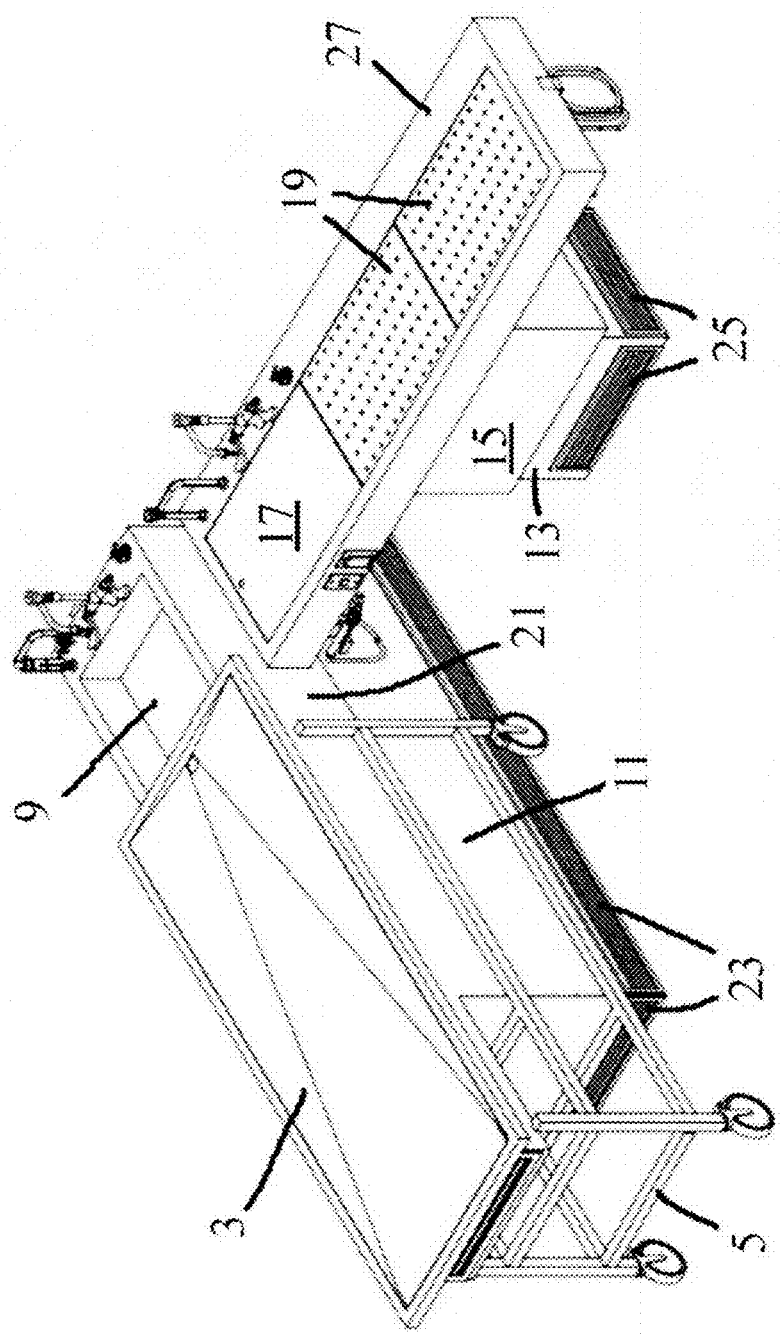
FIG. 9 is a perspective view of components of a system according to some embodiments.

FIG. 9 illustrates the same components and features as shown and described with reference to FIG. 7, but in this view the height of the top surface 7 (FIG. 1) of upper portion 21 with respect to the floor is seen to have been elevated as compared to its height depicted in FIG. 7 and FIG. 8. Selective up and down motion of upper portion 21 is accomplished in some embodiments by manually energizing an electrically-driven motor or hydraulic actuator effectively connected to a selectively height-raising and height-lowering mechanism disposed within the confines of base portion 11 and upper portion 21, as described elsewhere herein. In some embodiments this is accomplished by closing a switch. In some embodiments the switch is a double pole switch, enabling selective lowering or raising of upper portion 21 with respect to base portion 11.

Figure 10:
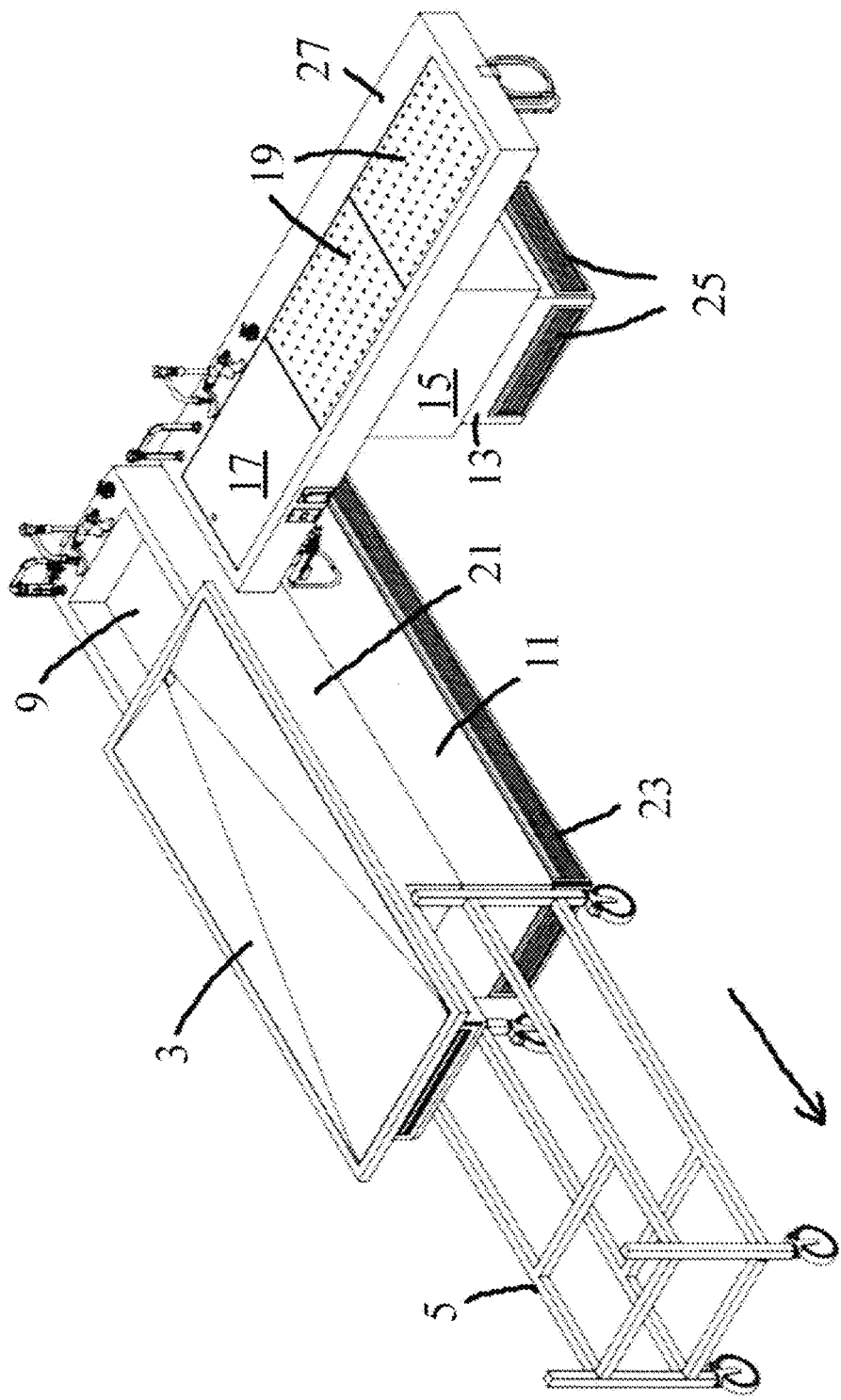
FIG. 10 is a perspective view of components of a system according to some embodiments.

Raising the height of upper portion 21 with respect to base portion 11 causes tray 3 to be fully supported by the top surface 7 of upper portion 21, thereby lifting it from the wheeled base 5 of gurney assembly 12. This permits wheeled base 5 again, to be wheeled away from corpse receiving station 10 (FIG. 1) as shown in FIG. 10 and FIG. 11.

Figure 11:
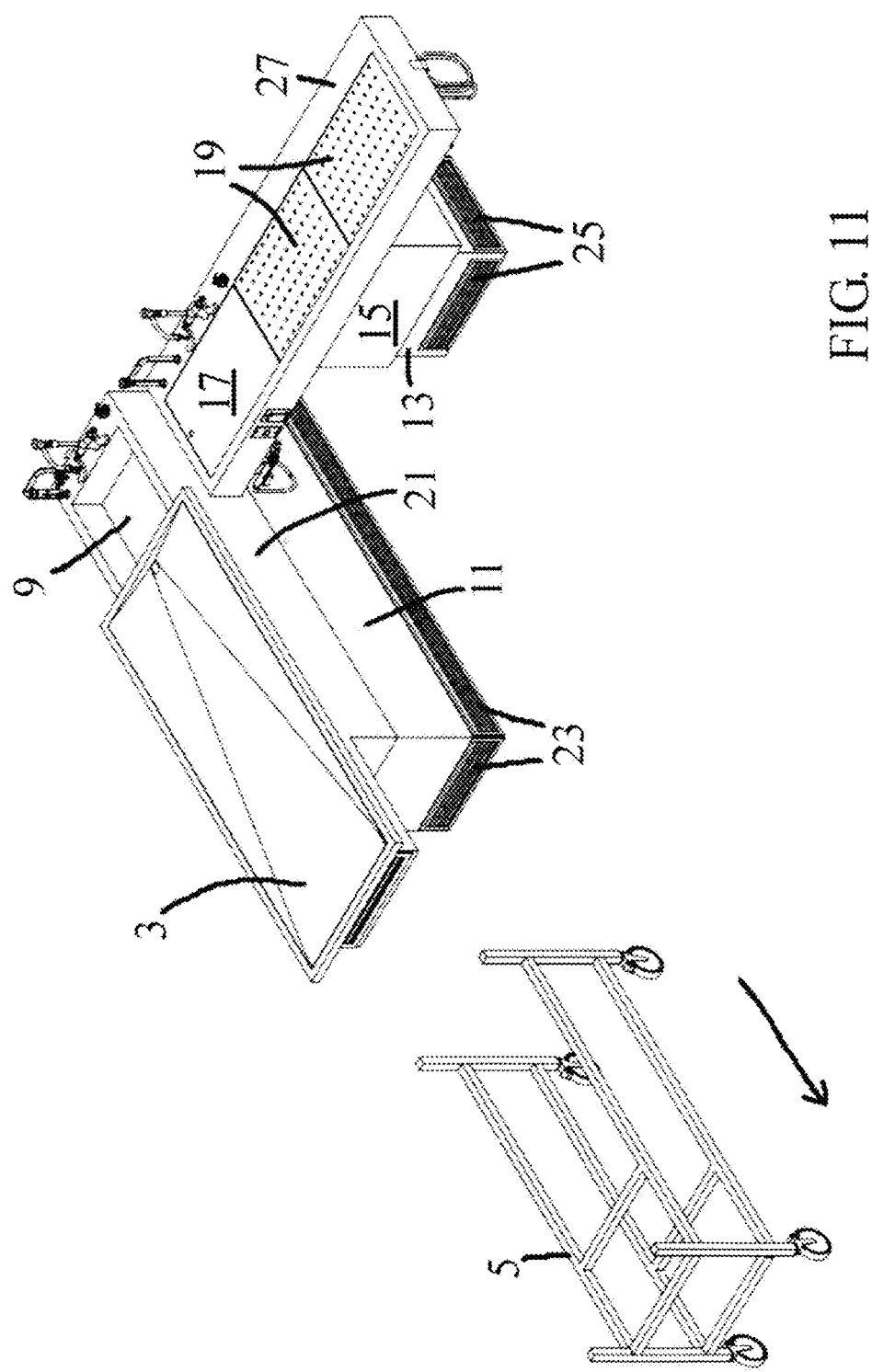
FIG. 11 is a perspective view of components of a system according to some embodiments.
Figure 12:
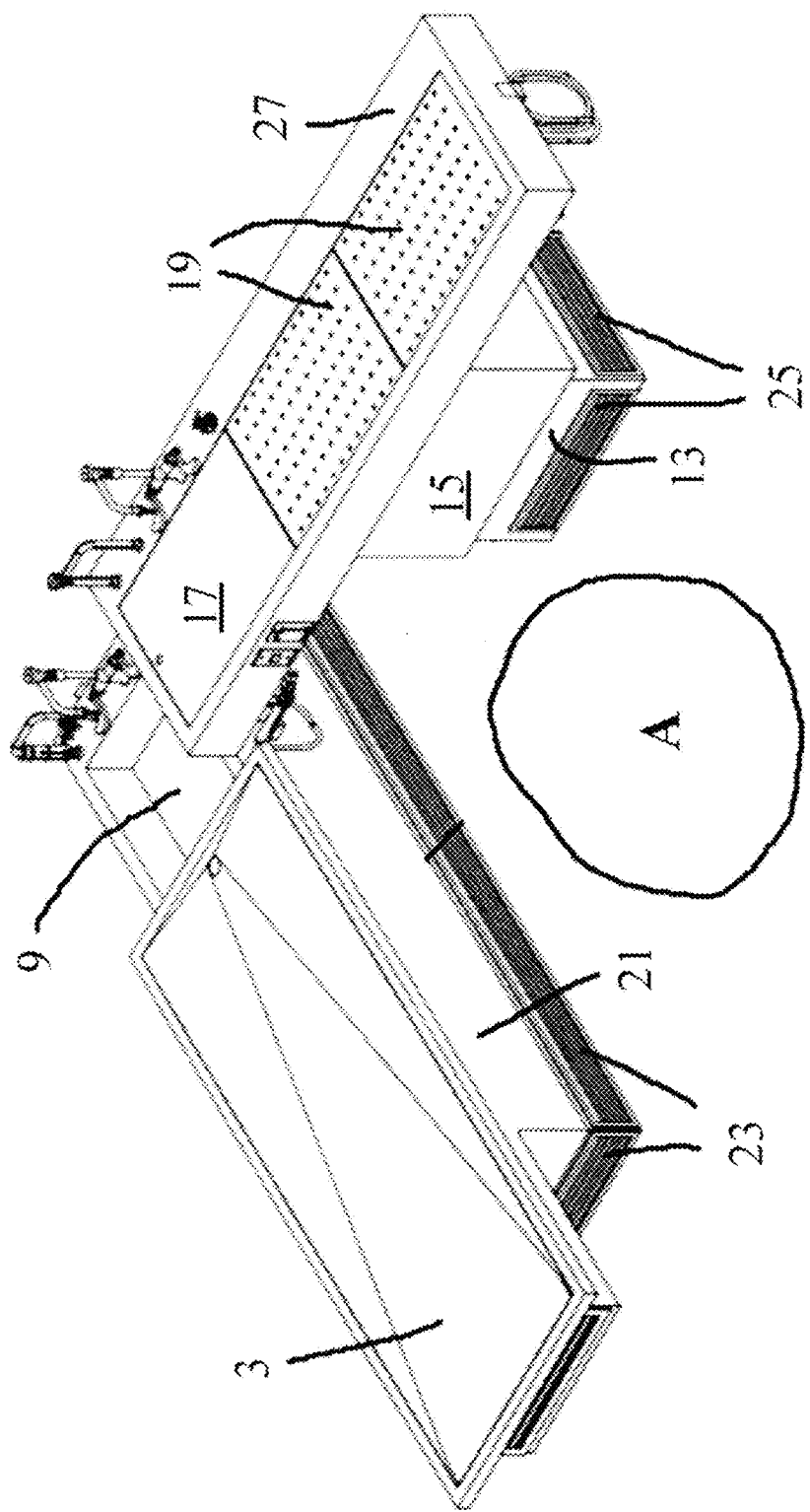
FIG. 12 is a perspective view of components of a system according to some embodiments.

FIG. 12 shows a system according to some embodiments of the instant technology, the wheeled base 5 having been withdrawn, and upper portion 21 now shown as having been lowered from its elevated position shown in FIG. 11 with respect to the elevation of the top surface of tabletop frame 27. This feature and its capability is advantageous for the pathologist, inasmuch as it eliminates the need for stepstools and the like often employed by pathologists, because not all pathologists are of the same physical height. This feature is also advantageous because many bariatric cases may be 24 inches high when laying flat on the back, making autopsy difficult for small stature pathologists. Lowering the corpse also makes taking evidential photos possible without the use of a ladder.

When using a system of this disclosure, the pathologist will typically dispose themselves or stand in an area denoted generally as area A in FIG. 12. This is advantageous for the practitioner when removing bodily organs from a corpse disposed on tray 3, since the removed organ can be placed on a weighing scale disposed on panel 17 merely by a twist of the practitioner's torso. This is also advantageous because no serological fluids are dripped onto the floor surface, facilitating easy post-autopsy clean-up operations.

Figure 13:
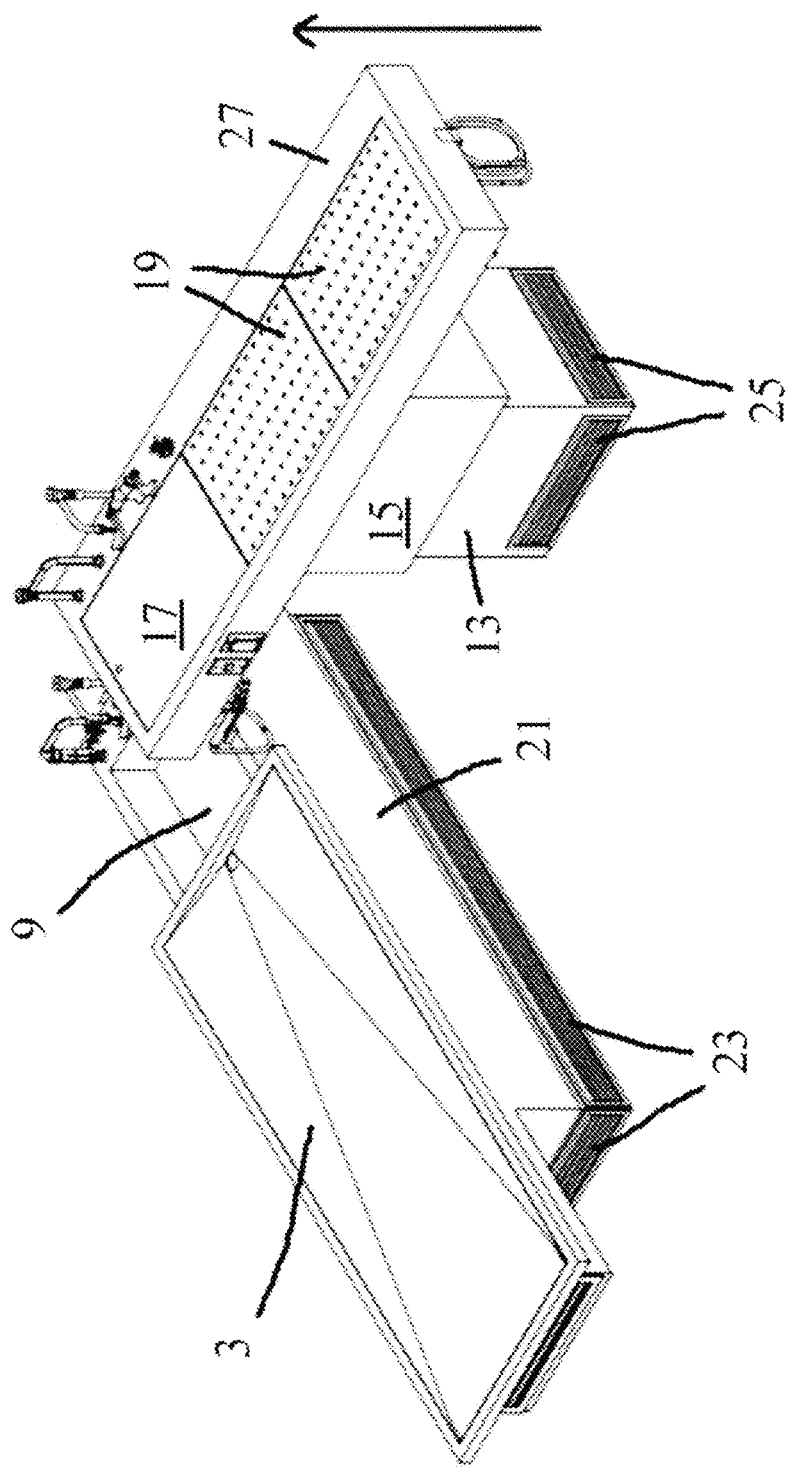
FIG. 13 is a perspective view of components of a system according to some embodiments.

Referring to FIG. 13, it is seen in this perspective view that the height of tabletop frame 27 has been elevated in the direction of the arrow shown with respect to its position depicted in FIG. 12. This is advantageous because a taller pathologist may work standing without bending over, which normally causes back pain. The tabletop height is adjustable to be just below the elbow of the pathologist to prevent liquids from running down the pathologists' arm and dripping from their elbow onto the floor surface.

Figure 14:
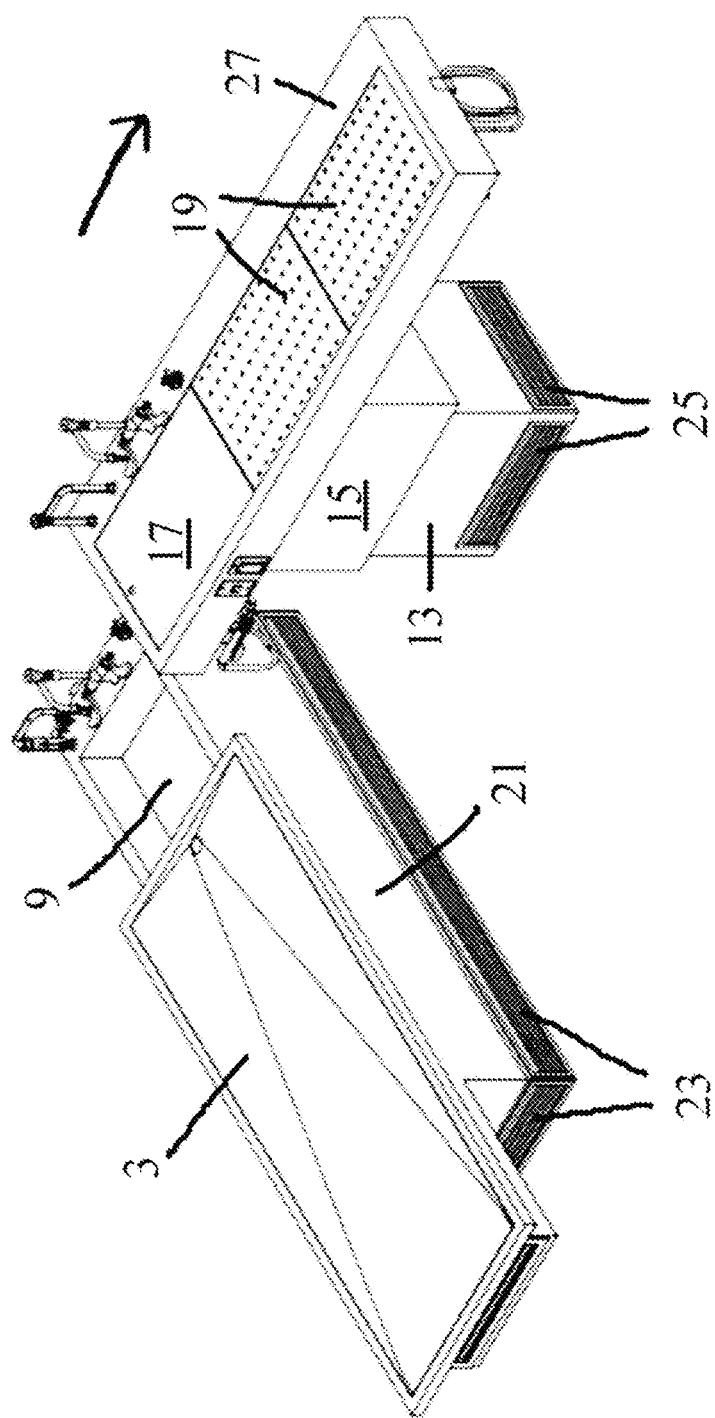
FIG. 14 is a perspective view of components of a system according to some embodiments.
Figure 15:
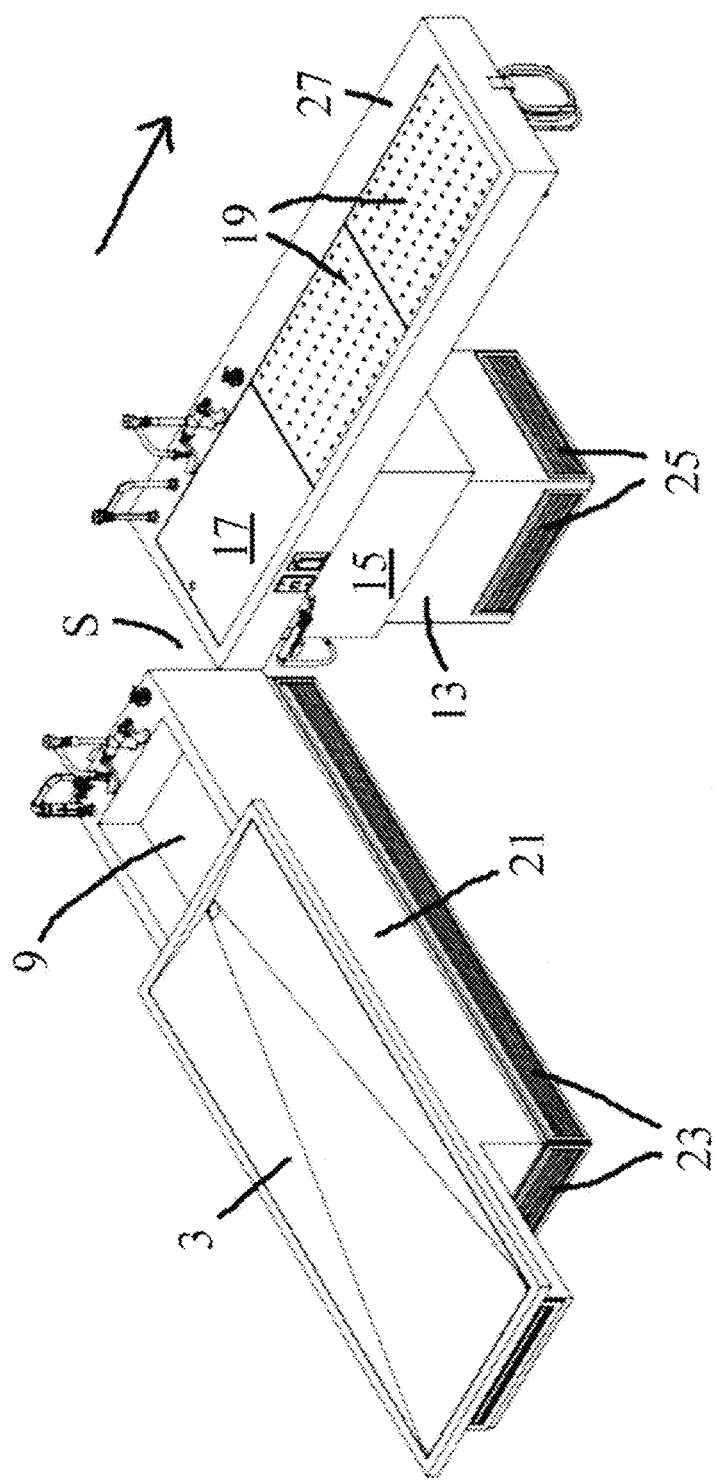
FIG. 15 is a perspective view of components of a system according to the instant technology in some embodiments.

In FIG. 14 is shown the lateral motion capability of tabletop frame 27 with respect to upper portion 15 of the organ dissecting station, in the direction of the arrow shown. The unit is also provided with capability of lateral motion in a direction opposite to that of the arrow. Lateral motion of tabletop 27 with respect to upper portion 15 of the organ dissecting station creates a space S, shown in FIG. 15. The creation of space S enables a practitioner 360 degree access to a corpse disposed on tray 3, which eliminates the necessity of having to walk all the way around an examination table. Yet, at the same time, the system provides for quick access to both the organs of a corpse disposed on tray 3 and a scale disposed on panel 17 when the system is selected to be configured as shown in FIG. 12.

In general, all organs of a body are removed during an autopsy and are typically weighed and themselves dissected further. A system of the instant technology greatly reduces the dripping of bodily fluids onto the floor surface in a post-mortem room, by having the source and destination of the organs to be in close proximity, unlike prior art systems in which the practitioner is required to walk significant distances holding an organ. The reduced drippage of fluids increases hygiene in the post-mortem room by limiting movement and transfer of biomass and fluids, while at the same time greatly reducing the creation of slippery areas on the floor, which is otherwise a safety hazard. At the same time, the selectively height adjustable feature of upper portion 21 of corpse-receiving station 10 eliminates the necessity for pathologists and technicians having to lift and move a corpse, as is required when using prior art systems.

Figure 16:
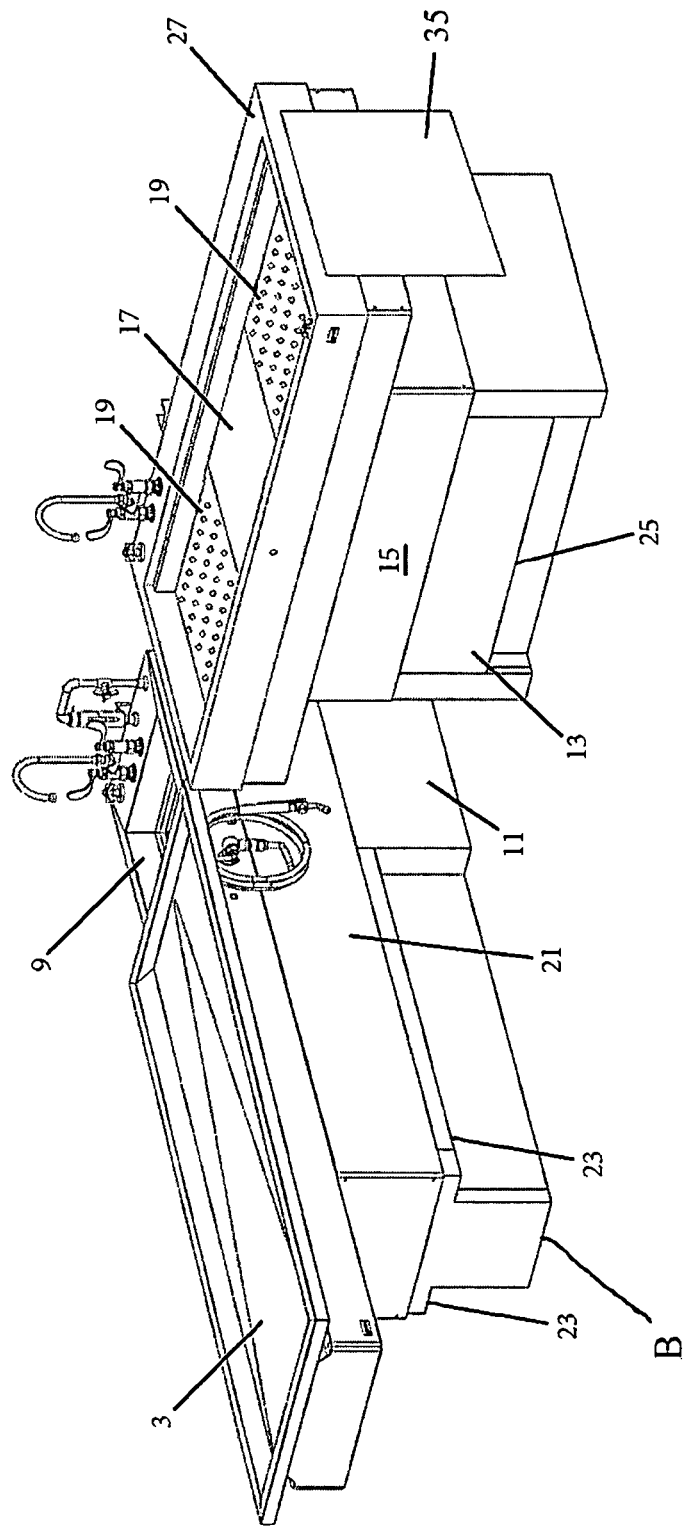
FIG. 16 is a perspective view of components of a system according to some alternate embodiments of the instant technology.
Figure 17:
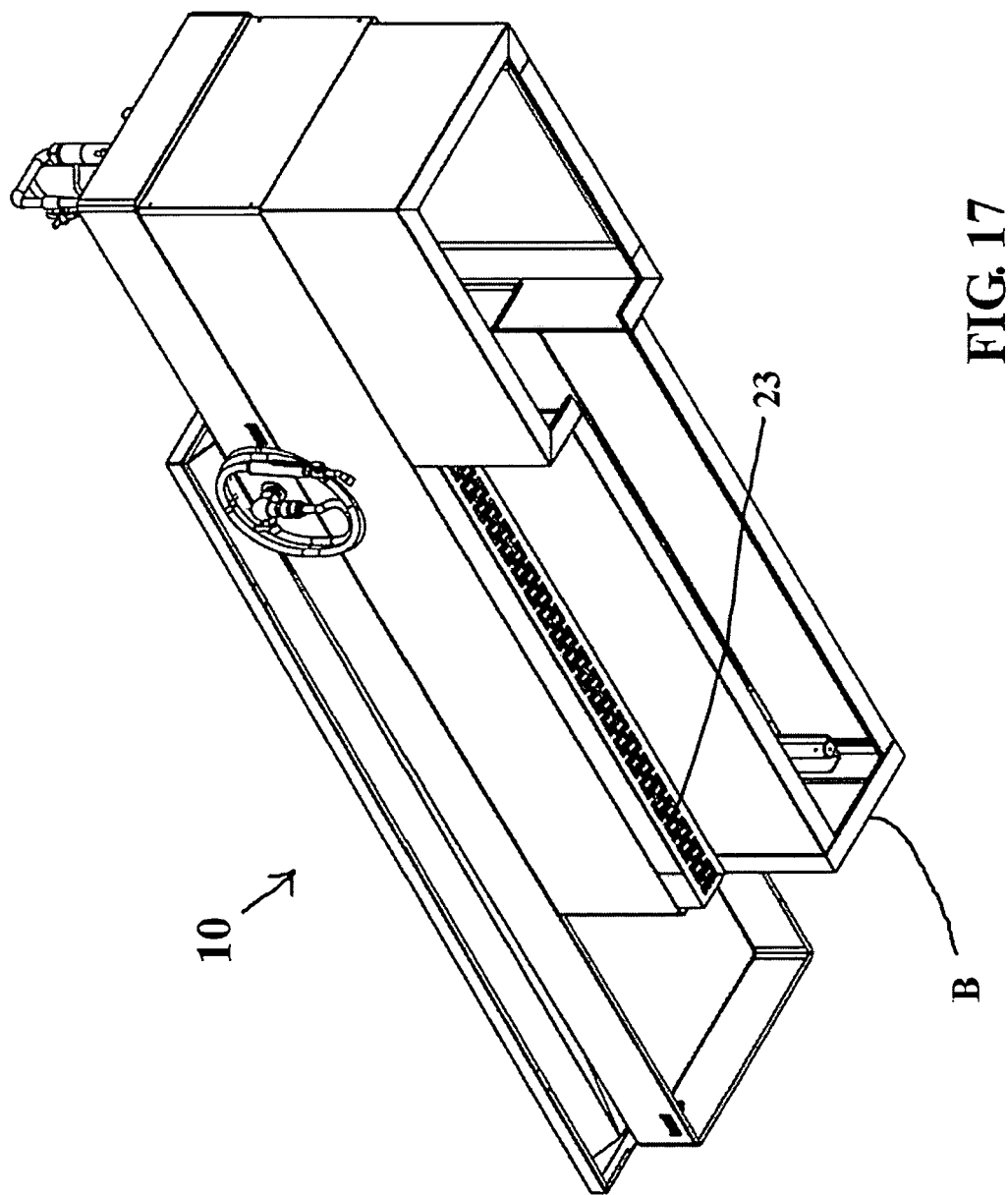
FIG. 17 is an underside perspective view of a corpse receiving station according to some alternate embodiments.

FIG. 16 shows a perspective view of components of a system according to some alternate embodiments of the instant technology in which a portion B of the base 11 of corpse receiving station 10 is contoured as shown to be more narrow from an end perspective than the remainder of base portion 11 as compared with embodiments shown and described in relation to FIG. 7. Such configuration provides that there is inherently present a "ceiling" above each of the indentations in the base portion of the corpse-receiving station. The underside perspective of FIG. 17 illustrates the narrowed contour, and the ceilings provide an alternate locations for the air intakes 23. This arrangement is advantageous inasmuch as such location for the ventilation air intake makes it essentially impossible for any liquids, spattered matter, etc. to enter the venting system, since the air intakes are oriented to be substantially horizontally planar and thus effectively shielded. A second vent 23 is present but not shown, which is identical to the vent 23 of FIG. 17 and is disposed analogously to the one vent shown and along the ceiling of the indented portion on the other side of the corpse receiving station. The indents present along each side of a substantial portion of the length of corpse receiving station 10 also simultaneously provide clearance for the wheels of gurney assembly 12 to fully rotate 360 degrees when a caster arrangement is provided. In some embodiments, the ventilation air intakes 23 are fitted with a conventional grating. FIG. 16 also includes a folding shelf 35, which in some embodiments features a photo blue poly board hingedly-attached to the organ dissecting station sufficiently that it can selectively be made to remain in a fixed horizontal position when desired.

Figure 18:
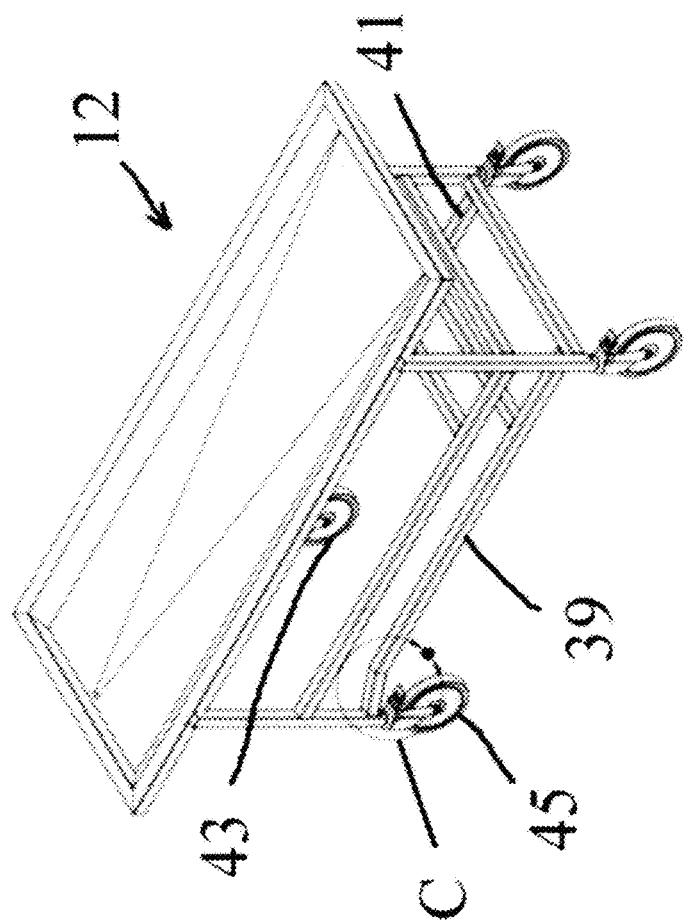
FIG. 18 is a perspective view of a gurney assembly according to some alternate embodiments.

In FIG. 18 is illustrated a gurney assembly 12 having frame rails 39, 41 as in some conventional gurneys. However, in some embodiments wheels 43, 45 are selected to be casters which are free to rotate 360 degrees about their Z-axis. Thus, when employing the gurney assembly of FIG. 18 to move a corpse, the gurney bearing such corpse is wheeled in the direction of the arrow in FIG. 7 until it attains the position shown in FIG. 8. When the gurney assembly is subsequently withdrawn in the direction of the arrow shown in FIG. 10, the indented regions of FIGS. 16, 17 provide clearance for casters or wheels 43, 45 to be fully rotatable about their Z-axis. This is found particularly advantageous when wheeling heavy corpses away from corpse receiving station 10. In some embodiments the frame portion of gurney assembly 12 of FIG. 18 is symmetrical with respect to a mirror plane present along the center of the longest length axis of the gurney assembly, when viewed from an overhead perspective.

Figure 19:
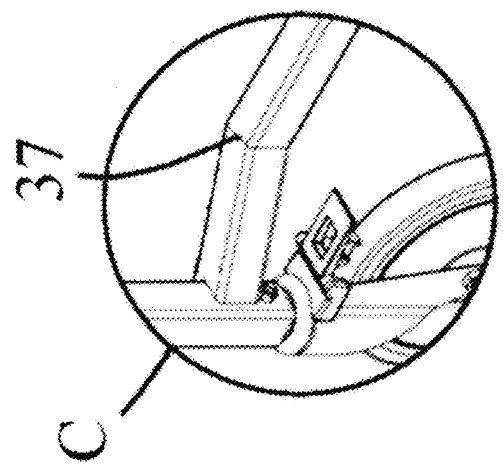
FIG. 19 is an enlarged perspective view of a portion of the gurney assembly of FIG. 18.
Figure 20:
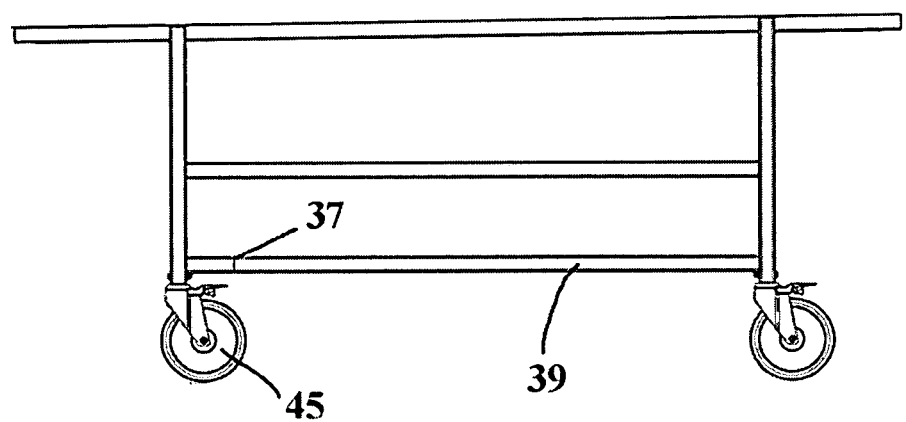

FIG. 18 illustrates how frame rails 39, 41 are not completely linear, but feature a bend 37 near the wheels or casters. Bend 37 is more closely illustrated in the enlargement C of FIG. 19. In some embodiments, an identical bend is present on frame rail 41 similarly near where the caster attaches to the frame of the gurney assembly. FIG. 20 is a side elevation view of the framework for a gurney assembly described with reference to FIG. 18 above, showing frame rail 39, wheel 45, and bend 37.

Figure 21:
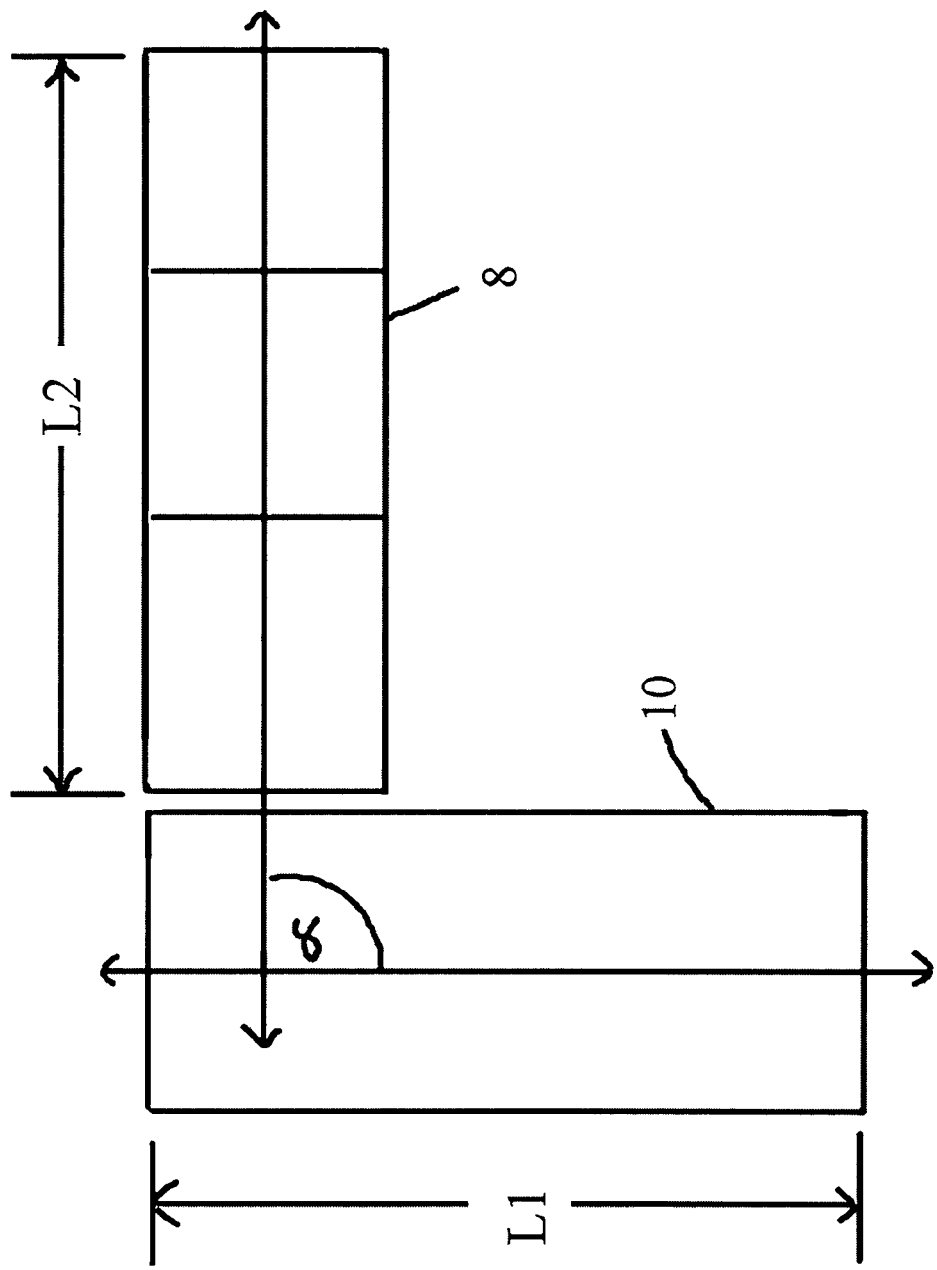
FIG. 21 is an overhead schematic view of orientation of components of a system according to some embodiments of the present technology.

FIG. 21 is an overhead schematic view of a system according to some embodiments of the current technology, showing the respective locations of corpse-receiving station 10 and organ dissecting station 8 in one particular possible configuration. In FIG. 21, each of corpse-receiving station 10 and organ dissecting station 8 have a longest length dimension, L1 and L2, respectively. Running parallel to each of L1 and L2, are shown centerlines of each of corpse-receiving station 10 and organ dissecting station 8. These centerlines can be considered as intersecting and defining an angle alpha (α), as shown. In some embodiments, angle alpha α is selected to be 90 degrees. In alternate embodiments, angle alpha α is selected to be greater than 90 degrees. In further alternate embodiments, angle alpha α is selected to be less than 90 degrees. It is within the scope of this disclosure to select angle alpha α to be any angle in the range of between seventy (70) and one hundred ten (110) degrees, including all degrees therebetween. Moreover, while each of corpse-receiving station 10 and organ dissecting station 8 are depicted as being generally rectangular as viewed from an overhead perspective, it is within the scope of the current technology for each of corpse-receiving station 10 and organ dissecting station 8 to independently be not rectangular as viewed from an overhead perspective. Any shape of these elements as viewed from an overhead perspective is within the scope of this disclosure, provided the functionality as taught herein is supported or maintained by whichever shape may be selected.

The mechanism by which corpse receiving station 10 can be selectively raised and lowered by a user is facilitated by upper portion 21 and base portion 11 being dimensioned and contoured sufficiently that base portion 11 is dimensioned slightly smaller than upper portion 21, and these components are arranged in a telescoping configuration. This enables upper portion 21 to essentially be slidably mounted about base portion 11.

In general, the motive means for providing upper portion 21 to be moved with respect to base portion 11 involves the presence of an electrical motor, which may be either a direct-current DC motor, or an alternating-current AC motor. Such motors have an armature which typically features a rotating output shaft, to which may be attached a pulley, gear, or other equivalently functioning output hardware. Motive energy is transmitted from the motor shaft through the output hardware and through a chain, belt, or direct contact with another gear, or linear gear, as in a rack and pinion arrangement. In some embodiments, the motor is rigidly attached to base portion 11, and in other embodiments the motor is rigidly attached to upper portion 21. In any event, selectively reversible up and down movement of upper portion 21 with respect to base portion 11 is achieved by energization of the motor, the selective reversibility of motion being controlled by the electrical current supplied to the motor using conventional switches, rheostats or other selected components, some embodiments employing means known to those skilled in the mechanical and electrical arts. Other useful arrangements for this purpose of motion of upper portion 21 with respect to base portion 11 is achieved by the use of one or more conventional hydraulic actuators.

The means by which organ dissection station 8 can be selectively raised and lowered by a user is facilitated by upper portion 15 and base portion 13 being dimensioned and contoured sufficiently that base portion 13 is dimensioned slightly smaller than upper portion 15, and these components are arranged in a telescoping configuration. This enables upper portion 15 to essentially be slidably mounted about base portion 13 analogously to the arrangement of base portion 11 and upper portion 21 on the corpse receiving station 10. The same components and arrangements useful for enabling motion of base portion 11 and upper portion 21 of the corpse receiving station 10 can be suitably employed for enabling like motion between the base portion 13 and upper portion 15 of organ dissecting station 8.

Moreover, the same components and arrangements useful for enabling motion of base portion 11 and upper portion 21 of the corpse receiving station 10 and between the base portion 13 and upper portion 15 of organ dissecting station 8 are useful for enabling the lateral motion of tabletop 27 with respect to upper portion 15 of organ dissecting station 8. Such lateral motion is enabled by the use of heavy duty manual slides, analogous or identical to sliding mechanisms used on drawers in furniture, file cabinets or a morgue. In some embodiments, the lateral movement is manually undertaken by hand, with conventional tabs being present as a locking-in-place mechanism. Any conventional known means for locking a sliding mechanism in a stationary position is suitable.

The fume evacuation or ventilation system employed with each of the organ dissecting station 8 and corpse-receiving station 10 each include air intakes 25 and 23 respectively. In most embodiments, these air intake vents are located as shown in the various figures, around the perimeters of base portions 11, 13; however, they may be disposed at any other location as deemed desirable by engineers. The ventilation systems for each of these components in some embodiments include a blower fan having an inlet and an outlet, the inlets being in effective fluid communication with the vents, and wherein the outlets of the blower fans direct the vaporous effluent into ducts present in the floor of the post-mortem room or other work area, these ducts ultimately being directed to the atmosphere outside the work area. In other embodiments, the ventilation system in the building in which the post-mortem room is located is used to evacuate the air.

Consideration must be given to the fact that although this invention has been described and disclosed in relation to certain preferred embodiments, equivalent modifications and alterations thereof may become apparent to persons of ordinary skill in this art after reading and understanding the teachings of this specification, drawings, and the claims appended hereto. The present disclosure includes subject matter defined by any combinations of any one or more of the features provided in this disclosure with any one or more of any other features provided in this disclosure. These combinations include the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. These combinations also include combination of the features and/or limitations of one or more of the independent claims with features and/or limitations of another independent claims to arrive at a modified independent claim, with the remaining dependent claims in their original text or as modified per the foregoing, being read and applied to any independent claim so modified. The present invention has been disclosed and claimed with the intent to cover modifications and alterations that achieve substantially the same result as herein taught using substantially the same or similar structures, being limited only by the scope of the claims which follow.

What is claimed is:

1. A system useful for performing medical examinations comprising:
   a) a corpse-receiving station having a longest length dimension, an end and an edge, and comprising a base portion and an upper portion having a flat top surface, said upper portion being selectively vertically-adjustable with respect to said base portion; and
   b) an organ dissecting station having a longest length dimension, an end and an edge, and comprising a base portion and an upper portion having a top surface, said upper portion being selectively vertically-adjustable with respect to said base portion and selectively horizontally-adjustable with respect to said base portion;

wherein said corpse-receiving station and said organ dissecting station are disposed in close proximity to one another, and oriented so that the longest length dimension of said corpse-receiving station and the longest length dimension of said organ dissecting section intersect one another at any selected angle in the range of between seventy and one hundred ten degrees; and wherein said upper portion of said organ dissecting station is selectively horizontally-adjustable to provide for creation of a space between said end of said organ dissecting station and said edge of said corpse-receiving station, said space being of sufficient dimension to enable a person to pass therethrough when walking.

2. The system according to claim 1, wherein said end of said organ dissecting station is facing said edge of said corpse-receiving station and wherein said edge of said organ dissecting station is substantially coincident with said end of said corpse-receiving station.

3. The system according to claim 1, wherein the angle of intersection of said longest length dimension of said organ dissecting station and said longest length dimension of said corpse-receiving station is about ninety degrees.

4. The system according to claim 1, wherein said upper portion of said corpse-receiving station comprises a basin disposed substantially at said end and adjacent to said flat top surface.

5. The system according to claim 1, wherein said top surface of said organ dissecting station includes a perforated surface.

6. The system according to claim 1, wherein said base portion of said corpse-receiving station comprises at least one air intake vent disposed substantially near a bottom of said base portion.

7. The system according to claim 1, wherein said base portion of said organ dissecting station comprises at least one air intake vent disposed substantially near a bottom of said base portion.

8. The system according to claim 1, further comprising a gurney assembly having a wheeled base and a tray disposed thereon, wherein said gurney assembly is disposed about said upper portion of said corpse-receiving station such that said top surface of said corpse-receiving station is in contact with said tray.

9. The system according to claim 8, wherein said tray is selectively detachable from said wheeled base.

10. The system according to claim 9, wherein said tray is selectively detached from said wheeled base by selectively vertically adjusting said upper portion of said corpse-receiving station upward so that said top surface of said corpse-receiving station lifts said tray from said wheeled base and wheeled base is capable of being removed from said corpse-receiving station.

11. The system according to claim 1, wherein said base portion of said corpse-receiving station includes indentations running laterally along each side thereof, wherein the indentations being sufficient to enable 360 degree rotation of casters present on a gurney assembly when a gurney assembly is present about said corpse-receiving station.

12. The system according to claim 11, wherein each of said indentations includes a ceiling portion, and wherein a ventilation air inlet is present along a length of each of said ceiling portions.

13. A method for examining and dissecting a corpse, comprising the steps of:

a) providing a system according to claim 10, wherein said tray has a corpse disposed thereon;

b) wheeling said gurney assembly sufficiently to provide said tray to be disposed above said top surface of said corpse-receiving station;

c) elevating said upper portion of said corpse-receiving station sufficiently to lift said tray from said wheeled base;

d) removing said wheeled base from its being about said corpse-receiving station;

e) examining said corpse with respect to any pertinent feature thereof;

f) causing said upper portion of said organ dissecting section to be moved horizontally, sufficiently to create an opening space between said organ dissecting section and said corpse-receiving section of sufficient dimension to enable a pathologist to pass through said space;

g) passing through said space; and h) further examining said corpse, wherein said examining said corpse optionally includes making at least one incision on said corpse.

14. The method according to claim 13, further comprising the step of:

i) removing any selected organ from said corpse.

15. A system useful for performing medical examinations comprising:

a corpse-receiving station including a base portion and an upper portion having a flat top surface, wherein the upper portion is selectively vertically-adjustable with respect to the base portion;

a gurney assembly having a wheeled base and a tray detachably disposed thereon, wherein the gurney assembly is capable of being disposed about the corpse-receiving station such that the tray is located over the upper portion of the corpse-receiving station, wherein the tray is capable of being detached from the wheeled base by vertically raising the upper portion of the corpse-receiving station to lift the tray from the wheeled base and enable the wheeled base to be removed; and an organ dissecting station including a base portion and an upper portion having a top surface, wherein the upper portion is selectively vertically-adjustable with respect to the base portion and selectively horizontally-adjustable with respect to said base portion.

16. The system of claim 15, wherein the corpse-receiving station and the organ dissecting station are disposed in close proximity to one another, wherein the upper portion of the organ dissecting station is selectively horizontally-adjustable to provide for creation of a space sufficient to enable a person to pass therethrough between the organ dissecting station and the corpse-receiving station.

17. The system of claim 15, wherein the upper portion of the corpse-receiving station includes a basin adjacent to the flat top surface.

18. The system of claim 15, wherein the top surface of the organ dissecting station includes a perforated surface.

19. The system of claim 15, further comprising at least one air intake vent disposed near bottom of at least one of the base portion of the corpse-receiving station and the base portion of the organ dissecting station.

20. The system of claim 15, wherein the base portion of the corpse-receiving station includes indentations running laterally along each side thereof, wherein the indentations enable 360-degree rotation of casters on the wheeled base of the gurney assembly.

21. The system of claim 20, wherein the indentations include a ceiling portion, and further comprising at least one ventilation air inlet disposed in ceiling portion of at least one of the indentations in the base portion of the corpse-receiving station.

* * * * *